(12) United States Patent  
Schuler

(10) Patent No.: US 8,467,869 B2  
(45) Date of Patent: *Jun. 18, 2013

(54) METHOD AND SYSTEM FOR MODULATING EATING BEHAVIOR BY MEANS OF NEURO-ELECTRICAL CODED SIGNALS

(76) Inventor: Eleanor L. Schuler, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/547,108

(22) Filed: Jul. 12, 2012

(65) Prior Publication Data

US 2012/0277837 A1 Nov. 1, 2012

Related U.S. Application Data

(60) Division of application No. 11/430,556, filed on May 8, 2006, which is a continuation-in-part of application No. 10/897,700, filed on Jul. 23, 2004, now abandoned.

(51) Int. Cl.
*A61N 1/00* (2006.01)
(52) U.S. Cl.
USPC .............................................. 607/2
(58) Field of Classification Search
USPC ........................ 607/45, 58, 48, 134, 135, 2
See application file for complete search history.

(56) References Cited

U.S. PATENT DOCUMENTS

| 5,188,104 | A | 2/1993 | Wernicke et al. |
| 5,263,480 | A | 11/1993 | Wernicke et al. |
| 5,540,730 | A * | 7/1996 | Terry et al. ............ 607/40 |
| 6,587,719 | B1 | 7/2003 | Barrett et al. |
| 6,832,114 | B1 | 12/2004 | Whitehurst et al. |
| 2002/0049482 | A1 | 4/2002 | Fabian et al. |
| 2004/0024428 | A1 | 2/2004 | Barrett et al. |
| 2005/0033376 | A1 | 2/2005 | Whitehurst |
| 2005/0049655 | A1 | 3/2005 | Boveja et al. |
| 2005/0240253 | A1 * | 10/2005 | Tyler et al. ............ 607/134 |

* cited by examiner

*Primary Examiner* — Niketa Patel
*Assistant Examiner* — Alyssa M Alter
(74) *Attorney, Agent, or Firm* — Kermit D. Lopez; Luis M. Ortiz; Ortiz & Lopez, PLLC

(57) ABSTRACT

A method for modulating eating behavior comprising (i) generating at least one confounding neuro-electrical signal that is adapted to modulate the sense of taste in the body, (ii) generating at least one confounding neuro-electrical signal that is adapted to modulate the sense of smell in the body, and (iii) transmitting at least one of the confounding neuro-electrical signals to a subject to modulate the subject's sense of taste or smell. In a preferred embodiment, both confounding neuro-electrical signals are transmitted to the subject to modulate the subject's sense of taste and smell.

18 Claims, 5 Drawing Sheets

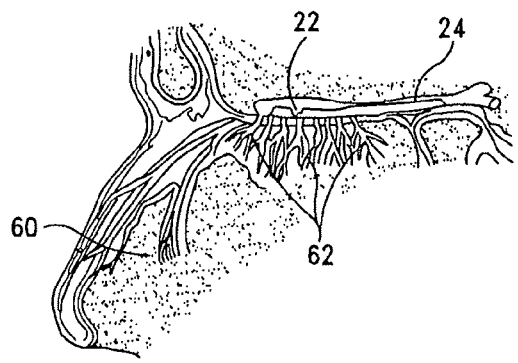
*FIG.—4A*
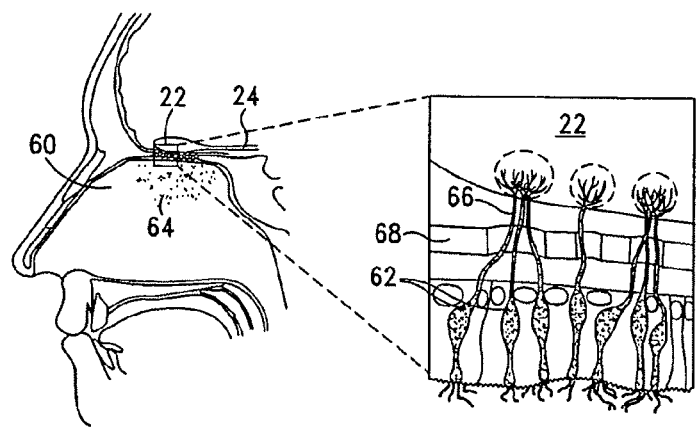
*FIG.—4B*
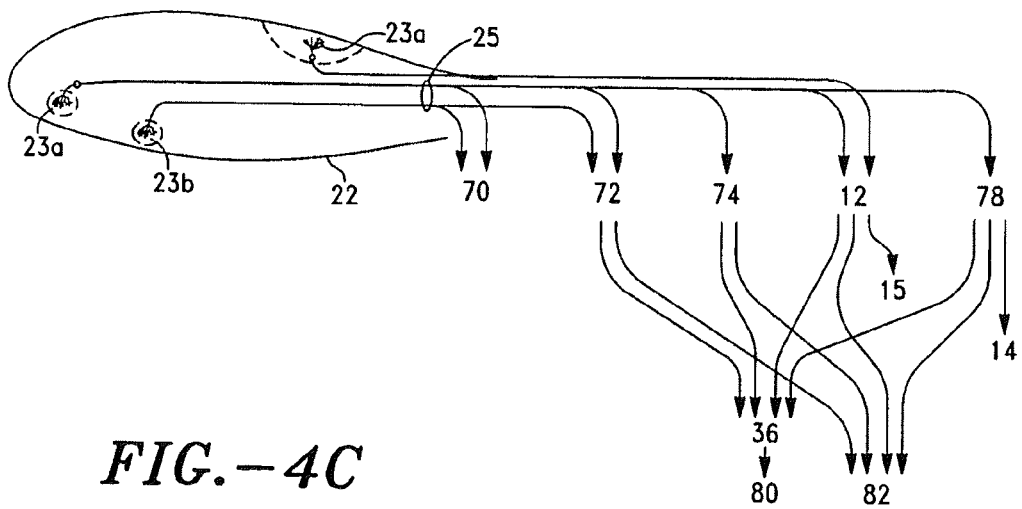
*FIG.—4C*

METHOD AND SYSTEM FOR MODULATING EATING BEHAVIOR BY MEANS OF NEURO-ELECTRICAL CODED SIGNALS

CROSS-REFERENCE TO PATENT APPLICATIONS

This patent application is a divisional of U.S. patent application Ser. No. 11/430,556 filed on May 8, 2006, entitled "Method and System for Modulating Eating Behavior by Means for Neuro-Electrical Coded Signals," which is hereby incorporated by reference in its entirety. U.S. patent application Ser. No. 11/430,556 is a Continuation-in-Part of U.S. patent application Ser. No. 10/897,700, which was filed on Jul. 23, 2004 now abandoned and is also incorporated herein by reference in its entirety. Thus, the present application traces its priority date to the Jul. 23, 2004 filing date of U.S. patent application Ser. No. 10/897,700.

TECHNICAL FIELD

Embodiments generally relate to medical methods and systems for controlling emotional and instinctual behavior. More particularly, the embodiments relate to modulating eating behavior by means of neuro-electrical coded signals.

BACKGROUND

As is well known in the art, the emotional and instinctual system of the human brain is commonly referred to as the "limbic system". The limbic system provides and controls inborn and acquired behavior. The limbic system is also the seat of instincts, emotions, and motivation.

The instinctual and emotional activity (or behavior) of the limbic system includes food and water intake, desire, and limits. Thus, the instinctual and emotional disorders relating thereto, such as compulsive overeating and other eating disorders, is associated with the limbic system.

As is also well known in the art, the brain modulates (or controls) limbic system via electrical signals (I.e., action potentials or neuro-electrical signals), which are transmitted through the nervous system. The nervous system includes two components: the central nervous system, which comprises the brain and the spinal cord, and the peripheral nervous system, which generally comprises groups of nerve cells (i.e., neurons) and peripheral nerves that lie outside the brain and spinal cord. The two systems are anatomically separate, but functionally interconnected.

As indicated, the peripheral nervous system is constructed of nerve cells (or neurons) and glial cells (or glia), which support the neurons. Operative neuron units that carry signals from the brain are referred to as "efferent" nerves. "Afferent" nerves are those that carry sensor or status information to the brain.

A typical neuron includes four morphologically defined regions: (i) cell body, (ii) dendrites, (iii) axon, and (iv) presynaptic terminals. The cell body (soma) is the metabolic center of the cell. The cell body contains the nucleus, which stores the genes of the cell, and the rough and smooth endoplasmic reticulum, which synthesizes the proteins of the cell.

The cell body typically includes two types of outgrowths (or processes): the dendrites and the axon. Most neurons have several dendrites; these branch out in tree-like fashion and serve as the main apparatus for receiving signals from other nerve cells.

The axon is the main conducting unit of the neuron. The axon is capable of conveying electrical signals along distances that range from as short as 0.1 mm to as long as 2 m. Many axons split into several branches, thereby conveying information to different targets.

Near the end of the axon, the axon is divided into fine branches that make contact with other neurons. The point of contact is referred to as a synapse. The cell transmitting a signal is called the presynaptic cell, and the cell receiving the signal is referred to as the postsynaptic cell. Specialized swellings on the axon's branches (i.e., presynaptic terminals) serve as the transmitting site in the presynaptic cell.

Most axons terminate near a postsynaptic neuron's dendrites. However, communication can also occur at the cell body or, less often, at the initial segment or terminal portion of the axon of the postsynaptic cell.

The electrical signals transmitted along the axon interact with the limbic system, referred to as action potentials, are rapid and transient "all-or-none" nerve impulses. Action potentials typically have an amplitude of approximately 100 millivolts (mV) and a duration of approximately 1 msec. Action potentials are conducted along the axon, without failure or distortion, at rates in the range of approximately 1-100 meters/sec. The amplitude of the action potential remains constant throughout the axon, since the impulse is continually regenerated as it traverses the axon.

A "neurosignal" is a composite signal that includes many action potentials. The neurosignal also includes an instruction set for proper system and organ function. A limbic system neurosignal would thus include an instruction set for chewing and swallowing of food, drinking of water, etc.

Neurosignals or "neuro-electrical coded signals" are thus codes that contain complete sets of information for complete system and organ function. As set forth in Co-Pending application Ser. No. 11/125,480, filed May 9, 2005, once these neurosignals, have been isolated, recorded and standardized, a nerve-specific neuro-electrical signal or instruction can be generated and transmitted to a subject to control the limbic system and, hence, treat a multitude of disorders associated therewith. The noted disorders include, but are not limited to, various eating disorders, such as compulsive overeating and obesity, bulimia, and anorexia nervosa.

The increasing prevalence of eating disorders, particularly obesity, in adults (and children) is one of the most serious and widespread health problems facing the world community. It is estimated that currently in American 55% of adults are obese and 20% of teenagers are either obese or significantly overweight. Additionally, 6% of the total population of the United States is morbidly obese.

This data is alarming for numerous reasons, not the least of which is it indicates an obesity epidemic. Many health experts believe that obesity is the first or second leading cause of preventable deaths in the United States, with cigarette smoking either just lagging or leading.

It is the consequences of being overweight that are most alarming. Obesity is asserted to be the cause of approximately eighty percent of adult onset diabetes in the United States, and of ninety percent of sleep apnea cases. Obesity is also a substantial risk factor for coronary artery disease, stroke, chronic venous abnormalities, numerous orthopedic problems, and esophageal reflux disease. More recently, researchers have documented a link between obesity, infertility, and miscarriages, as well as post menopausal breast cancer.

Despite these statistics, treatment options for obese people are limited. Classical models combining nutritional counseling with exercise and education have not led to long term success for very many patients. Use of liquid diets and pharmaceutical agents may result in weight loss which, however, is only rarely sustained. Surgical procedures that cause either gastric restriction or malabsorption have been, collectively, the most successful long-term remedy for severe obesity. However, this type of surgery involves a major operation, can lead to emotional problems, and cannot be modified readily as patient needs demand or change.

Various "electrical stimulation" apparatus, systems, and methods have also been employed to treat compulsive overeating and obesity. Illustrative are the systems and methods disclosed in U.S. Pat. Nos. 5,263,480 and 6,587,719, and U.S. Pat. Application Publications 2005/0033376 A1 and 2004/0024428 A1.

The noted "electrical stimulation" systems and methods, as well as most known systems, primarily involve the transmission of electrical impulses to a subject to induce a feeling of nausea and, hence, discourage food intake by the subject.

It has, however, been recently found that those afflicted with ageosia (i.e, loss of taste) or anosmia (i.e. loss of smell) typically suffer from a persistent loss of appetite and/or desire to eat. Modulating (or blocking) the sense of taste and/or the sense of smell in a subject thus provides an effective means for controlling eating behavior of the subject and, hence, treating various eating disorders, particularly, compulsive overeating.

It would thus be desirable to provide a method and system for modulating eating behavior that includes means for generating and transmitting confounding neuro-electrical signals to a subject that are adapted to modulate the subject's sense of taste and/or smell, i.e., confound the naturally generated neuro-electrical signals and thereby restrict the transfer of information associated with the sense of taste and smell to the brain. It would also be desirable to provide a method and system for modulating eating behavior that includes means for generating and transmitting simulated neuro-electrical signals to a subject that are adapted to induce or enhance the subject's sense of taste and/or smell.

It is, therefore, an object of the present invention to provide a method and system for modulating eating behavior that overcomes the drawbacks associated with prior art methods and systems for regulating eating behaviors.

It is another object of the invention to provide a method and system for modulating eating behavior that includes means for generating at least one confounding neuro-electrical signal that is adapted to confound at least one neuro-electrical signal that is generated in the body and associated with the sense of taste, and thereby restrict the transfer of information associated therewith to the brain when transmitted to the subject.

It is another object of the invention to provide a method and system for modulating eating behavior that includes means for generating at least one confounding neuro-electrical signal that is adapted to confound at least one neuro-electrical signal that is generated in the body and associated with the sense of smell, and thereby restrict the transfer of information associated therewith to the brain when transmitted to the subject.

It is another object of the invention to provide a method and system for modulating eating behavior that includes means for generating at least one simulated neuro-electrical signal that is adapted to induce or enhance the sense of taste when transmitted to a subject.

It is another object of the invention to provide a method and system for modulating eating behavior that includes means for generating at least one simulated neuro-electrical signal that is adapted to induce or enhance the sense of smell when transmitted to a subject.

It is another object of the invention to provide a method and system for modulating eating behavior that includes means for monitoring food intake or consumption of a subject.

It is another object of the invention to provide a method and system for modulating eating behavior that includes means for transmitting confounding or simulated neuro-electrical signals to a subject to modulate the subject's sense of taste and smell in response to the subject's food intake exceeding or falling below a predetermined threshold level.

It is another object of the invention to provide a method and system for modulating eating behavior that includes means for timed transmission of confounding or simulated neuro-electrical signals to a subject, whereby the subject's sense of taste and/or sense of smell is modulated.

It is another object of the invention to provide a method and system for modulating eating behavior that can be effectively employed to treat various eating disorders, including, without limitation, compulsive eating and obesity, bulimia and anorexia nervosa.

BRIEF SUMMARY

The following summary is provided to facilitate an understanding of some of the innovative features unique to the disclosed embodiments and is not intended to be a full description. A full appreciation of the various aspects of the embodiments disclosed herein can be gained by taking the entire specification, claims, drawings, and abstract as a whole.

In accordance with the above objects and those that will be mentioned and will become apparent below, in one embodiment of the invention, the method for modulating eating behavior of a subject includes the steps of (i) generating at least one confounding neuro-electrical signal that is adapted to modulate the sense of taste in the body, and (ii) transmitting the confounding neuro-electrical signal to the subject.

In one embodiment, the modulation comprises restricting the transmission of afferent information to the brain that is generated in the body and associated with the sense of taste.

In another embodiment, the modulation comprises substantially abating the transmission of afferent information to the brain that is generated in the body and associated with the sense of taste.

In one embodiment, the confounding neuro-electrical signal is transmitted to the subject at predetermined time intervals.

In one embodiment, the confounding neuro-electrical signal is transmitted to the subject manually.

In another embodiment, the confounding neuro-electrical signal is transmitted to the subject manually and at predetermined time intervals.

In yet another embodiment, a plurality of confounding neuro-electrical signals is transmitted to the subject.

In accordance with another embodiment of the invention, the method for modulating eating behavior of a subject includes the steps of (i) generating at least one simulated neuro-electrical signal that is adapted to modulate the sense of taste in the body, and (ii) transmitting the simulated neuro-electrical signal to the subject.

Preferably, the simulated neuro-electrical signal substantially corresponds to or is representative of a neuro-electrical signal that is generated in the body.

In one embodiment, the modulation comprises inducing the sense of taste in the subject's body.

In another embodiment, the modulation comprises enhancing the sense of taste in the subject's body.

In one embodiment, the simulated neuro-electrical signal is transmitted to the subject at predetermined time intervals.

In one embodiment, the neuro-electrical signal is transmitted manually to the subject.

In another embodiment, the simulated neuro-electrical signal is transmitted to the subject manually and at predetermined time intervals.

In yet another embodiment, a plurality of simulated neuro-electrical signals is transmitted to the subject.

In accordance with another embodiment of the invention, the method for modulating eating behavior of a subject includes the steps of (i) generating at least one confounding neuro-electrical signal that is adapted to modulate the sense of smell in the body, and (ii) transmitting the confounding neuro-electrical signal to the subject.

In one embodiment, the modulation comprises restricting the transmission of afferent information to the brain that is generated in the body and associated with the sense of smell.

In another embodiment, the modulation comprises substantially abating the transmission of afferent information to the brain that is generated in the body and associated with the sense of smell.

In one embodiment, the confounding neuro-electrical signal is transmitted to the subject at predetermined time intervals.

In one embodiment, the confounding neuro-electrical signal is transmitted to the subject manually.

In another embodiment, the confounding neuro-electrical signal is transmitted to the subject manually and at predetermined time intervals.

In yet another embodiment, a plurality of confounding neuro-electrical signals is transmitted to the subject.

In accordance with another embodiment of the invention, the method for modulating eating behavior of a subject includes the steps of (i) generating at least one simulated neuro-electrical signal that is adapted to modulate the sense of smell in the body, and (ii) transmitting the simulated neuro-electrical signal to the subject.

Preferably, the simulated neuro-electrical signal substantially corresponds to or is representative of a neuro-electrical signal that is generated in the body.

In one embodiment, the modulation comprises inducing the sense of smell in the subject's body.

In another embodiment, the modulation comprises enhancing the sense of smell in the subject's body.

In one embodiment, the simulated neuro-electrical signal is transmitted to the subject at predetermined time intervals.

In one embodiment, the neuro-electrical signal is transmitted manually to the subject.

In another embodiment, the simulated neuro-electrical signal is transmitted to the subject manually and at predetermined time intervals.

In yet another embodiment, a plurality of simulated neuro-electrical signals is transmitted to the subject.

In another embodiment of the invention, the method for modulating eating behavior of a subject includes the steps of (i) generating at least one confounding neuro-electrical signal that is adapted to modulate the sense of taste in the body, (ii) sensing food intake in the subject over at least a first period of time, and (iii) transmitting the confounding neuro-electrical signal to the subject.

In one embodiment, the modulation comprises restricting the transmission of afferent information to the brain that is generated in the body and associated with the sense of smell.

In another embodiment, the modulation comprises substantially abating the transmission of afferent information to the brain that is generated in the body and associated with the sense of smell.

In one embodiment, the confounding neuro-electrical signal is transmitted to the subject if the food intake of the subject exceeds a predetermined threshold level during the first period of time.

In one embodiment, the confounding neuro-electrical signal is transmitted to the subject at predetermined time intervals.

In another embodiment, the confounding neuro-electrical signal is transmitted manually to the subject.

In yet another embodiment, a plurality of confounding neuro-electrical signals is transmitted to the subject.

In another embodiment of the invention, the method for modulating eating behavior of a subject includes the steps of (i) generating at least one simulated neuro-electrical signal that is adapted to modulate the sense of taste in the body, (ii) sensing food intake in the subject over at least a first period of time, and (iii) transmitting the simulated neuro-electrical signal to the subject.

Preferably, the simulated neuro-electrical signal substantially corresponds to or is representative of a neuro-electrical signal that is generated in the body.

In one embodiment, the modulation comprises inducing the sense of taste in the subject's body.

In another embodiment, the modulation comprises enhancing the sense of taste in the subject's body.

In one embodiment, the simulated neuro-electrical signal is transmitted to the subject if the food intake of the subject falls below a predetermined threshold level during the first period of time.

In one embodiment, the simulated neuro-electrical signal is transmitted to the subject at predetermined time intervals.

In another embodiment, the simulated neuro-electrical signal is transmitted manually to the subject.

In yet another embodiment, a plurality of simulated neuro-electrical signals is transmitted to the subject.

In another embodiment of the invention, the method for modulating eating behavior of a subject includes the steps of (i) generating at least one confounding neuro-electrical signal that is adapted to modulate the sense of smell in the body, (ii) sensing food intake in the subject over at least a first period of time, and (iii) transmitting the confounding neuro-electrical signal to the subject.

In one embodiment, the modulation comprises restricting the transmission of afferent information to the brain that is generated in the body and associated with the sense of smell.

In another embodiment, the modulation comprises substantially abating the transmission of afferent information to the brain that is generated in the body and associated with the sense of smell.

In one embodiment, the confounding neuro-electrical signal is transmitted to the subject if the food intake of the subject exceeds a predetermined threshold level during the first period of time.

In one embodiment, the confounding neuro-electrical signal is transmitted to the subject at predetermined time intervals.

In another embodiment, the confounding neuro-electrical signal is transmitted manually to the subject.

In another embodiment of the invention, the method for modulating eating behavior of a subject includes the steps of (i) generating at least one simulated neuro-electrical signal that is adapted to modulate the sense of smell in the body, (ii)

sensing food intake in the subject over at least a first period of time, and (iii) transmitting the simulated neuro-electrical signal to the subject.

Preferably, the simulated neuro-electrical signal substantially corresponds to or is representative of a neuro-electrical signal that is generated in the body.

In one embodiment, the modulation comprises inducing the sense of smell in the subject's body.

In another embodiment, the modulation comprises enhancing the sense of smell in the subject's body.

In one embodiment, the simulated neuro-electrical signal is transmitted to the subject if the food intake of the subject falls below a predetermined threshold level during the first period of time, In one embodiment, the simulated neuro-electrical signal is transmitted to the subject at predetermined time intervals, In another embodiment, the simulated neuro-electrical signal is transmitted manually to the subject.

In yet another embodiment, a plurality of simulated neuro-electrical signals is transmitted to the subject.

In each of the noted embodiments, the confounding and simulated neuro-electrical signals are transmitted to the subject's nervous system.

In some embodiments, confounding and simulated neuro-electrical signals adapted to modulate the sense of taste are transmitted to the subject's glossopharyngeal nerve (cranial nerve IX).

In sonic embodiments, confounding and simulated neuro-electrical signals adapted to modulate the sense of smell are transmitted to the subject's Olfactory nerve complex.

In one embodiment of the invention, the step of transmitting a confounding or simulated neuro-electrical signal to the subject is accomplished by direct conduction or transmission through unbroken skin at a zone adapted to communicate with a target nerve, e,g., glossopharyngeal nerve. Such zone will preferably approximate a position close to the nerve or nerve plexus onto which the signal is to be imposed.

In an alternate embodiment of the invention, the step of transmitting a confounding or simulated neuro-electrical signal to the subject is accomplished by direct conduction via attachment of an electrode to the receiving nerve or nerve plexus. This requires a surgical intervention to physically attach the electrode to the selected target nerve.

In yet another embodiment of the invention, the step of transmitting a confounding or simulated neuro-electrical signal to the subject is accomplished by transposing the waveform signal into a seismic form in a manner that allows the appropriate "nerve" to receive and obey the coded instructions of the seismic signal.

According to the invention, a single confounding or simulated neuro-electrical signal or a plurality of confounding or simulated neuro-electrical signals can be transmitted to the subject in conjunction with one another.

The system for modulating eating behavior, in accordance with one embodiment of the invention, generally comprises (i) a processor adapted to generate at least one confounding or simulated neuro-electrical signal that is adapted to modulate the sense of taste in the body, and (ii) a signal transmitter adapted to be in communication with a subject's body for transmitting confounding and simulated neuro-electrical signals to the subject.

In another embodiment of the invention, the system for modulating eating behavior comprises (i) a processor adapted to generate at least one confounding or simulated neuro-electrical signal that is adapted to modulate the sense of smell in the body, and (ii) a signal transmitter adapted to be in communication with a subject's body for transmitting confounding and simulated neuro-electrical signals to the subject.

In another embodiment of the invention, the system for modulating eating behavior comprises (i) at least a first food intake sensor adapted to monitor the food intake of a subject and provide at least a first food intake signal indicative of the food intake, (ii) a processor in communication with the food intake sensor adapted to receive the first food intake signal, the processor being further adapted to generate at least one confounding or simulated neuro-electrical signal that is adapted to modulate the sense of taste in the body, and (iii) a signal transmitter adapted to be in communication with the subject's body for transmitting confounding and simulated neuro-electrical signals to the subject.

In another embodiment of the invention, the system for modulating eating behavior comprises (i) at least a first food intake sensor adapted to monitor the food intake of a subject and provide at least a first food intake signal indicative of the food intake, (ii) a processor in communication with the food intake sensor adapted to receive the first food intake signal, the processor being further adapted to generate at least one confounding or simulated neuro-electrical signal that is adapted to modulate the sense of smell in the body, and (iii) a signal transmitter adapted to be in communication with the subject's body for transmitting confounding and simulated neuro-electrical signals to the subject.

BRIEF DESCRIPTION OF THE DRAWINGS

The accompanying figures, in which like reference numerals refer to identical or functionally-similar elements throughout the separate views and which are incorporated in and form a part of the specification, further illustrate the present disclosed embodiments and, together with the detailed description herein, serve to explain the principles of the disclosed embodiments.

FIGS. 4A and 4B are illustrations of the nasal structures and nerves associated with the sense of smell;

FIG. 4C is a schematic illustration of the transfer of olfactory information from the olfactory bulb to the various structures of the brain;

DETAILED DESCRIPTION

The particular values and configurations discussed in these non-limiting examples can be varied and are cited merely to illustrate at least one embodiment and are not intended to limit the scope thereof.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a," "an" and "the" include plural referents unless the content clearly dictates otherwise. Thus, for example, reference to "a waveform signal" includes two or more such signals; reference to "a respiratory disorder" includes two or more such disorders and the like.

Definitions

Figure 1:
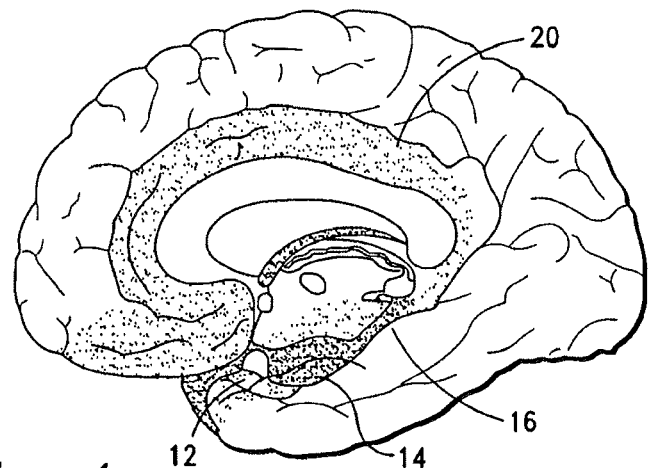
FIG. 1 is a medial view of a brain, showing the pre-frontal limbic cortex and limbic lobe.
Figure 2:
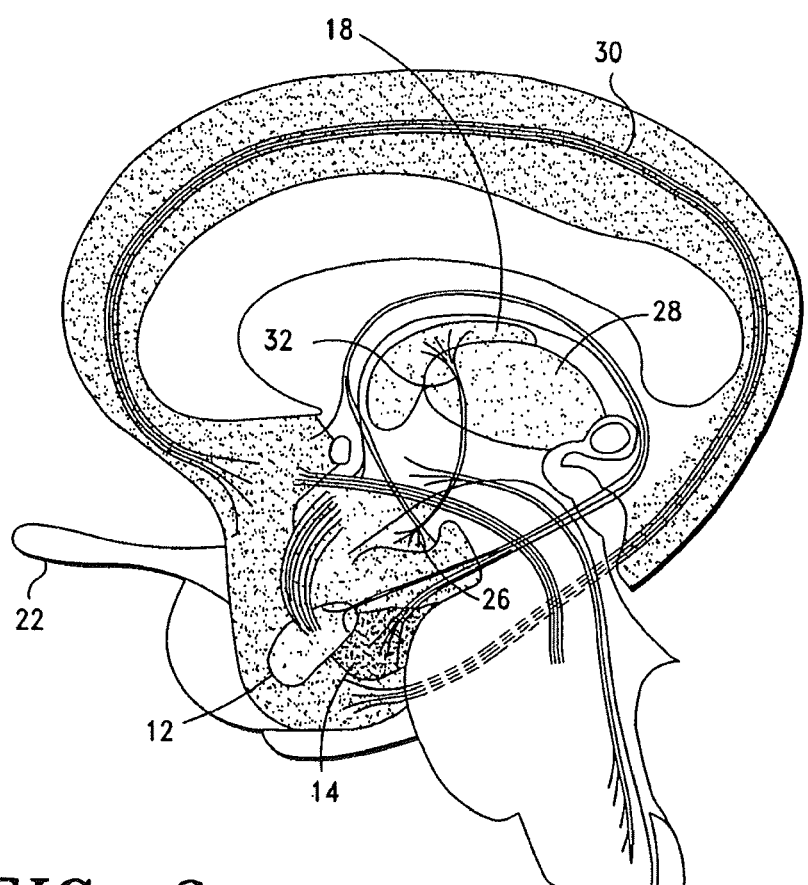
FIG. 2 is a further medial view of the brain, showing the deep-lying structures of the limbic system.

The term "limbic system", as used herein, means and includes, the grouping of subcortical structures (i.e., limbic lobe and cortex) disposed proximate the brain stem 10, including, without limitation, the amygdale 12, hippocampus 14, hypothalamus 15, parahippocampal gyrus 16, anterior thalamic nuclei 18, cingulate gyrus 20, olfactory bulb 22, mammillary body 26, medial dorsal nucleus of thalamus 28, cingulum 30, and mammillothalamic tract 32 (see FIGS. 1 and 2).

The term "nervous system", as used herein, means and includes the central nervous system, including the spinal cord, medulla oblongata, pons, cerebellum, midbrain, diencephalon and cerebral hemisphere, and the peripheral nervous system, including the neurons and glia.

The term "plexus", as used herein, means and includes a branching or tangle of nerve fibers outside the central nervous system.

The term "ganglion", as used herein, means and includes a group or groups of nerve cell bodies located outside the central nervous system.

The term "waveform signal" and "neuro-electrical signal", as used herein, mean and include a composite electrical signal that is generated in the body and carried by neurons in the body, including neurocodes, neurosignals and components and segments thereof, and generated neuro-electrical signals that substantially correspond thereto.

The term "simulated neuro-electrical signal", as used herein, means a neuro-electrical signal that produces or enhances the sense of taste or sense of smell in a subject when transmitted thereto.

The term "confounding neuro-electrical signal", as used herein, means and includes a neuro-electrical signal that is adapted to confound neuro-electrical signals that are generated in the body and are associated with the sense of taste and/or sense of smell, i.e., restrict the transfer of afferent information to the brain that is associated with the sense of taste and/or smell.

The term "eating disorder", as used herein, means and includes, without limitation, compulsive eating and obesity, bulimia and anorexia nervosa.

The term "eating disorder", as used herein, means and includes compulsive overeating and obesity, bulimia and anorexia nervosa.

The terms "patient" and "subject", as used herein, mean and include humans and animals.

The present invention substantially reduces or eliminates the disadvantages and drawbacks associated with prior art methods and systems for modulating or controlling eating behavior. In accordance with one embodiment of the invention, the method for modulating eating behavior of a subject includes the steps of (i) generating at least one confounding neuro-electrical signal that is adapted to modulate the sense of taste in the body, and (ii) transmitting the neuro-electrical signal to the subject.

In one embodiment, the modulation comprises restricting the transmission of afferent information to the brain that is generated in the body and associated with the sense of taste. In another embodiment, the modulation comprises substantially abating the transmission of afferent information to the brain that is generated in the body and associated with the sense of taste.

In accordance with another embodiment of the invention, the method for modulating eating behavior of a subject includes the steps of (i) generating at least one confounding neuro-electrical signal that is adapted to modulate the sense of smell in the body, and (ii) transmitting the confounding neuro-electrical signal to the subject.

In one embodiment, the modulation comprises restricting the transmission of afferent information to the brain that is generated in the body and associated with the sense of smell. In another embodiment, the modulation comprises substantially abating the transmission of afferent information to the brain that is generated in the body and associated with the sense of smell.

In some embodiments, the method for modulating eating behavior of a subject includes the steps of (i) generating at least one confounding neuro-electrical signal that is adapted to modulate the sense of taste in the body, (ii) generating at least one confounding neuro-electrical signal that is adapted to modulate the sense of smell in the body, and (ii) transmitting at least one of the confounding neuro-electrical signals to the subject to modulate the subject's sense of taste or smell. In a preferred embodiment, both confounding neuro-electrical signals are transmitted to the subject to modulate the subject's sense of taste and smell.

Figure 3A:
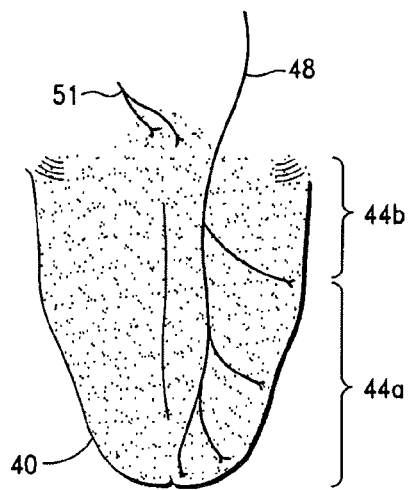
FIG. 3A is a plan view of a tongue, showing the innervation of the glossopharyngeal and chorda tympani nerves.
Figure 3B:
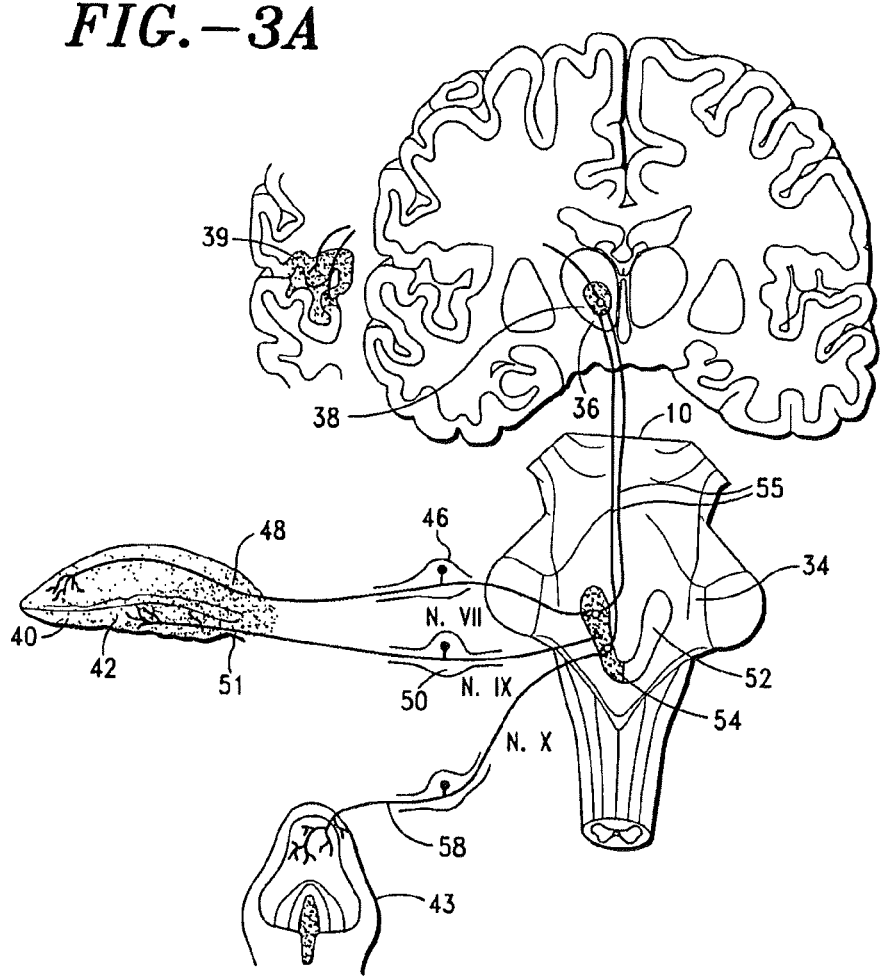
FIG. 3B is an illustration of the structures and nerves associated with the sense of taste, and the communication thereof from the tongue to the brain.

Referring now to FIGS. 3A and 3B, there is shown the structures and nerves that are associated with the sense of taste. As is well known in the art, the sense of taste originates in taste cells that are clustered in taste buds on the tongue 40, palate, pharynx 43, epiglottis, and upper third of the esophagus. On the tongue 40 taste buds are located primarily in the papillae, which are embedded in the epithelium 42.

As illustrated in FIGS. 3A and 3B, taste buds in the anterior two-thirds of the tongue (designated 44a) are innervated by sensory neurons of the geniculate ganglion 46, whose peripheral branches travel in the chords tympani nerve 48; a branch of the facial nerve, i.e., cranial nerve VII and its associated intermediate nerve. Taste buds in the posterior third of the tongue (designated 44b) are innervated by sensory neurons of the petrosal ganglion 50, whose peripheral branches travel in the lingual branch of the glossopharyngeal nerve 51, i.e. cranial nerve IX. Taste buds on the palate are innervated by the greater superficial petrosal branch of cranial nerve VII. The taste buds on the pharynx, epiglottis and esophagus are innervated by the superior laryngeal branch of cranial nerve X 58. Some of the noted nerves also carry somatosensory afferents that innervate regions of the tongue 40 surrounding taste buds.

The sensory fibers that receive input from the taste buds (and run in cranial nerves VII, IX and X) enter the nucleus of the solitary tract 52 in the medulla oblongata 34 where they form synapses on a thin column of cells in the gustatory area 54 of the rostral and lateral part of the nucleus of the solitary tract 52.

As illustrated in FIG. 3B, neurons in the gustatory area 54 (designated 55) project to the thalamus 36, where they terminate in the small cell (parvocellular) region of the ventral posterior medial nucleus 38. Neurons in the parvocellulular region of the thalamus that receive taste input project to neurons along the border between the anterior insula and the frontal perculium is the ipsilateral cerebal cortex 39.

Referring now to FIGS. 4A-4C, the structures and nerves associated with the sense of smell will now be discussed in detail. The initial events in olfactory perception occur in olfactory sensory nerves or neurons 62 in the nasal cavity 60. These neurons are embedded in the olfactory epithelium 64, a small patch of specialized epithelium that in humans covers a region in roof of the nasal cavity 60. The sensory neurons 62 project axons 66 to the olfactory bulb 22, which rests on the cribriform plate 68 of the ethmoid bone.

The human olfactory epithelium 64 contains several million olfactory sensory neurons 62 interspersed with glia-like supporting cells, both of which lie above a basal layer of stem cells. Olfactory neurons 62 are distinctive among neurons in that they are short-lived, with an average life span of only approx. 30 days, and are continuously replaced from the basal stem cell population.

Referring now to FIG. 4C, the axons and dendrites of the granule mitral and tufted relay neurons (designated 23*a*, 23*b*, respectively) of the olfactory bulb 22 project through the lateral olfactory tract 25 to the olfactory cortex. The olfactory cortex, defined as that portion of the cortex that receives a direct projection from the olfactory bulb 22, is divided into five main areas: (i) the anterior olfactory nucleus 70, which connects the two olfactory bulbs 22 through a portion of the anterior commissure; (ii) the piriform cortex 74; (iii) parts of the amygdale 12, (iv) the olfactory tubercle 72; and (v) part of the entorhinal cortex 78. From the latter four areas, information is relayed to the orbitofrontal cortex 80 via the thalamus 36; however, the olfactory cortex also makes direct contacts with the frontal cortex 82. In addition, olfactory information is transmitted from the amygdale 12 to the hypothalamus 15 and from the entorhinal area to the hippocampus 14.

According to the invention, the confounding neuro-electrical signals of the invention can be adapted to restrict or substantially abate the transmission of afferent information to the brain that is generated in the body and associated with the sense of taste or smell. Thus, in the case of a compulsive eating event by a subject, when a confounding neuro-electrical signal that is adapted to modulate the subject's sense of taste is transmitted to the subject, the confounding satiety signal would restrict or abate the transmission of afferent information associated with the sense of taste to the brain (and limbic system), rendering the subject partially or, more preferably, substantially fully ageusic. When a confounding neuro-electrical signal that is adapted to modulate the subject's sense of smell is transmitted to the subject, the confounding neuro-electrical signal would restrict or abate the transmission of afferent information associated with the sense of smell to the brain, rendering the subject partially or, more preferably, substantially fully anosmic.

As is well known in the art, a subject that is ageusic and/or anosmic typically losses the desire to eat.

According to the invention, the confounding neuro-electrical signals can comprise various forms and can be adapted to modulate or modify naturally generated neuro-electrical signals in numerous ways. By way of example, in one envisioned embodiment of the invention, at least one portion of the confounding neuro-electrical signal comprises a substantially negative mirror image of at least one portion of the naturally generated neuro-electrical signal, whereby when the confounding neuro-electrical signal is transmitted to a subject a portion of the naturally generated neuro-electrical signal is modified, e.g., amplitude of the signal and, hence, reduced sense of taste or smell.

In another envisioned embodiment of the invention, the confounding neuro-electrical signal is adapted to substantially confound the naturally generated neuro-electrical signal when transmitted to a subject, i.e., restrict or abate the transmission of afferent information embodied in the neuro-electrical signal to the brain.

One suitable confounding neuro-electrical signal is described in Co-Pending U.S. application Ser. No. 11/393,194; which is incorporated by reference herein.

It will further be appreciated by one having ordinary skill in the art that the degree or magnitude of the sense of taste and sense of smell can also be modulated by transmitting confounding (and simulated neuro-electrical) signals to selective nerves in a subject's body.

In another embodiment of the invention, the method for modulating eating behavior of a subject includes the steps of (i) generating at least one simulated neuro-electrical signal that is adapted to modulate the sense of taste in the body, and (ii) transmitting the simulated neuro-electrical signal to the subject. In a preferred embodiment, the simulated neuro-electrical signal substantially corresponds to or is representative of a neuro-electrical signal that is generated in the body.

In one embodiment, the modulation comprises inducing the sense of taste in the subject's body. In another embodiment, the modulation comprises enhancing the sense of taste in the subject's body.

In another embodiment of the invention, the method for modulating eating behavior of a subject includes the steps of (i) generating at least one simulated neuro-electrical signal that is adapted to modulate the sense of smell in the body, and (ii) transmitting the simulated neuro-electrical signal to the subject. In a preferred embodiment, the simulated neuro-electrical signal similarly substantially corresponds to or is representative of a neuro-electrical signal that is generated in the body.

In one embodiment, the modulation comprises inducing the sense of smell in the subject's body. In another embodiment, the modulation comprises enhancing the sense of smell in the subject's body.

As is also well known in the art, inducing or enhancing the sense of taste and/or smell will enhance a subject's desire to eat.

In some embodiments, the method for modulating eating behavior also includes the step of monitoring the subject's food intake, i.e., the quantity of food consumed. One suitable means for monitoring or ascertaining food intake comprises implanting one or more sensing electrodes in or at the esophagus to detect the passage of food as the subject swallows. The swallows are then summed over a predetermined time interval to estimate the amount of food consumed in that interval. According to the invention, a confounding neuro-electrical signal that is adapted to modulate the sense of taste or smell or a plurality of confounding signals that are adapted to modulate the sense of taste and smell can then be transmitted to the subject if the estimated food consumption exceeds a predetermined threshold level.

Since the caloric intake of similar volumes (or quantities) of two different foods can be significantly different, in one envisioned embodiment of the invention, the method of monitoring (or ascertaining) a subject's food intake includes ascertaining the approximate caloric intake. One suitable means of ascertaining the calories associated with a quantity of selected foods is to include a table of foods and associated calories or, more preferably, calories per weight or volume, in the control system module or processor (which are described below).

The subject would then input the meal (or desired food) that is about to be consumed into the system and the system would determine the caloric value associated with each inputted food. Based on a preprogrammed caloric intake, or more preferably, a caloric intake over a predetermined period of time, which is tailored to the subject, the system would determine a target, desired range of food intake for the inputted food(s).

Alternatively, the target calories and, hence, volume of food intake can be determined from various nutritional formulae or a standardized caloric table. By way of example, referring to TABLE I (discussed below), there is shown a table of estimated amounts of calories needed to maintain energy balance for various gender and age groups at three different levels of physical activity. The noted levels are based on Estimated Energy Requirements (EER) from the Institute of Medicine Dietary Reference Intakes macronutrients report, 2002; calculated by gender, age, and activity level for reference-sized individuals.

"Reference size", as determined by IOM, is based on median height and weight for ages up to age 18 years of age and median height and weight for that height to give a BMI of 21.5 for adult females and 22.5 for adult males. For more information, please refer to "TABLE I" shown in paragraph [0154] of U.S. Patent Application Publication No. 200610206169A1, which published on Sep. 14, 2006, and is based on U.S. patent application Ser. No. 11/430,556, which is incorporated herein by reference in its entirety. Definitions of "sedentary," "moderately active", and "active" are also included in U.S. patent application Ser. No. 11/430,556 with respect to TABLE I.

According to the invention, the caloric intake and, hence, quantity of food (i.e., food intake) can be adjusted upward or downward to induce weight loss or weight gain.

Thus, in one embodiment of the invention, the method for modulating eating behavior of a subject includes the steps of (i) generating at least one confounding neuro-electrical signal that is adapted to modulate the sense of taste in the body, (ii) sensing food intake in the subject over at least a first period of time, and (iii) transmitting the confounding neuro-electrical signal to the subject.

In one embodiment, the confounding neuro-electrical signal is transmitted to the subject if the food intake of the subject exceeds a predetermined threshold level during the first period of time. According to the invention, when the confounding neuro-electrical signal is transmitted to the subject, the subject loses the sense of taste, i.e., is rendered ageusic, and loses the desire to eat at a predetermined level of food consumption that is sufficient to maintain physiologic needs, but supportive of weight reduction.

In another embodiment of the invention, the method for modulating eating behavior of a subject includes the steps of (i) generating at least one confounding neuro-electrical signal that is adapted to modulate the sense of smell in the body, (ii) sensing food intake in the subject over at least a first period of time, and (iii) transmitting the confounding neuro-electrical signal to the subject.

In one embodiment, the confounding neuro-electrical signal is similarly transmitted to the subject if the food intake of the subject exceeds a predetermined threshold level during the first period of time. According to the invention, when the noted confounding neuro-electrical signal is transmitted to the subject, the subject loses the sense of smell, i.e. is rendered anosmic, and similarly loses the desire to eat.

The noted methods of the invention can thus be effectively employed to treat obesity and control excessive overeating. Similar methods can also be employed to treat bulimia.

In another embodiment of the invention, the method for modulating eating behavior of a subject includes the steps of (i) generating at least one simulated neuro-electrical signal that is adapted to modulate the sense of taste in the body, (ii) sensing food intake in the subject over at least a first period of time, and (di) transmitting the simulated neuro-electrical signal to the subject. According to the invention, the modulation can comprise inducing or enhancing the sense of taste in the subject's body.

In yet another embodiment of the invention, the method for modulating eating behavior of a subject includes the steps of (i) generating at least one simulated neuro-electrical signal that is adapted to modulate the sense of smell in the body, (ii) sensing food intake in the subject over at least a first period of time, and (id) transmitting the simulated neuro-electrical signal to the subject. According to the invention, the modulation can comprise inducing or enhancing the sense of smell in the subject's body.

According to the invention, when the noted simulated neuro-electrical signals are transmitted to the subject, the subject experiences a desire to eat.

The noted methods can thus be effectively employed to treat anorexia nervosa. The methods can also be employed to modify or control food consumption after various surgical procedures.

In alternative embodiments of the invention, the methods include the pre-programmed or timed transmission of either a confounding or simulated neuro-electrical signal. For example, in the case of an obese or bulimic subject, a confounding neuro-electrical signal can be transmitted at set intervals at, near and/or between customary meal times to render the subject ageusic or anosmic. In the case of an anorexic subject, a simulated neuro-electrical signal can be transmitted at prescribed meal times to enhance to desire to eat.

As discussed in detail herein, alternatively, or in addition with sensing food intake and transmitting a confounding or simulated neuro-electrical signal in response thereto and/or timed transmission of a confounding or simulated neuro-electrical signal, the transmission of the confounding and simulated neuro-electrical signals can also be accomplished manually. As will be appreciated by one having skill in the art, manual transmission of a confounding or simulated signal is useful in situations where the subject has an earnest desire to control his or her eating behavior, but requires supportive measures due to insufficient will power to refrain from compulsive and/or damaging behavior.

In some embodiments of the invention, the method for modulating eating behavior includes the steps of capturing at least one neuro-electrical signal from a body that is associated with the sense of taste and/or at least one neuro-electrical signal from the body that is associated with the sense of smell.

According to the invention, neuro-electrical signals associated with the sense of taste can be captured or transmitted into cranial nerves V (trigeminal nerve), VII (facial nerve), including the intermediate nerve and chords typani nerve, IX (glossopharyngeal), X (vagus) and XII (hypoglossal). Neuro-electrical signals associated with the sense of smell can be captured or transmitted into cranial nerves I (olfactory), IX (glossopharyngeal), including the olfactory tract. The signals can also be collected directly from nerves associated with the limbic system.

Methods and systems for capturing coded signals from the nerve(s), and for storing, processing and transmitting neuro-electrical signals are set forth in Co-Pending U.S. application Ser. No. 10/000,005, filed Nov. 20, 2001, U.S. application Ser. No. 11/125,480, filed May 9, 2005, and U.S. application Ser. No. 11/147,497,filed Jun. 7, 2005; which are incorporated by reference herein in their entirety.

In accordance with one embodiment of the invention, neuro-electrical signals that are generated in the body and associated with the sense of taste and/or smell are captured and transmitted to a processor or control module. Preferably, the control module includes storage means adapted to store the captured signals.

According to the invention, the captured neuro-electrical signals can be processed by known means and a simulated neuro-electrical signal that is representative of or substantially similar to at least one neuro-electrical signal that is generated in the body or a captured neuro-electrical signal can be generated by the control module. The noted neuro-electrical signal is similarly stored in the storage means of the control module.

Further details of the processor, control module and processing means are set forth in Co-Pending U.S. application Ser. No. 11/147,497, filed Jun. 7, 2005; which is incorporated herein in its entirety.

In response to a pre-programmed event, e.g., food intake exceeding a predetermined threshold level, food intake falling below a predetermined threshold level, a pre-programmed period of time or time interval or manual activation, a generated confounding neuro-electrical signal or simulated neuro-electrical signal is accessed from the storage means and transmitted to the subject via a transmitter (or probe).

According to the invention, the applied voltage of confounding neuro-electrical signals and simulated neuro-electrical signals can be up to 20 volts to allow for voltage loss during the transmission of the signals. Preferably, current is maintained to less than 2 amp output.

Figure 5:
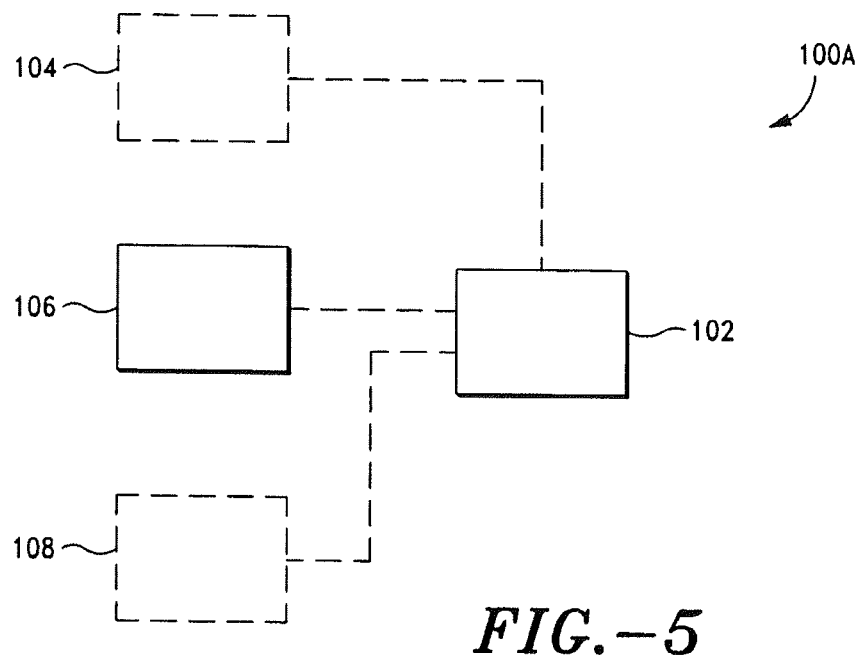
FIG. 5 is a schematic illustration of one embodiment of a taste modulation system, according to the invention.

Referring now to FIG. 5, there is shown a schematic illustration of one embodiment of a taste modulation system 100A of the invention. According to the invention, the smell modulation systems of the invention include the same components and subsystems as the taste modulation system 100A. The following disclosure relating to various embodiments of the taste modulation system will thus be equally applicable to the smell modulation systems of the invention.

As illustrated in FIG. 5, the system 100A includes a control module 102, which is adapted to receive neuro-electrical signals from a signal sensor (shown in phantom and designated 104) that is in communication with a subject, and at least one treatment member 106.

The control module 102 is further adapted to generate confounding neuro-electrical signals and simulated neuro-electrical signals that substantially correspond to or are representative of neuro-electrical signals that are generated in the body, and transmit the simulated neuro-electrical signals and confounding neuro-electrical signals to the treatment member 106 at predetermined periods of time (or time intervals). The control module 102 is also adapted to transmit the simulated neuro-electrical signals and confounding neuro-electrical signals to the treatment member 106 manually, i.e. upon activation of a manual switch (not shown).

The treatment member 106 is adapted to communicate with the body and receives the confounding neuro-electrical signals and simulated neuro-electrical signals from the control module 102. According to the invention, the treatment member 106 can comprise an electrode, antenna, a seismic transducer, or any other suitable form of conduction attachment for transmitting the confounding neuro-electrical signals and simulated neuro-electrical signals to a subject.

According to the invention, the treatment member 106 can be attached to appropriate nerves via a surgical process. Such surgery can, for example, be accomplished through a "keyhole" entrance in an endoscopic procedure. If necessary, a more invasive procedure can be employed for more proper placement of the treatment member 106.

As illustrated in FIG. 5, the control module 102 and treatment member 104 can be entirely separate elements, which allow system 100A to be operated remotely. According to the invention, the control module 102 can be unique, i.e., tailored to a specific operation and/or subject, or can comprise a conventional device.

Figure 6:
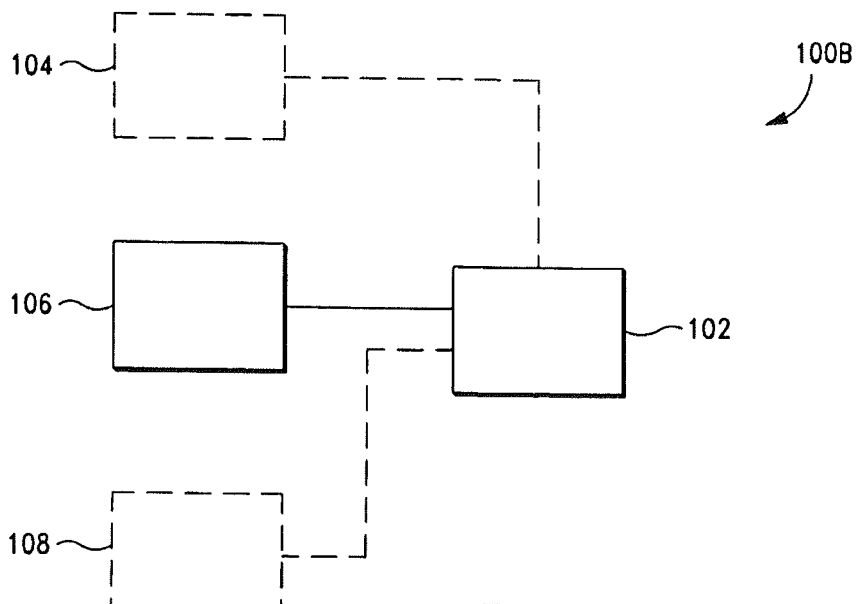
FIG. 6 is a schematic illustration of another embodiment of a taste modulation system, according to the invention.

Referring now to FIG. 6, there is shown a further embodiment of a taste modulation system 100B of the invention. As illustrated in FIG. 6, the system 100B is similar to system 100A shown in FIG. 5. However, in this embodiment, the control module 102 and treatment member 106 are connected.

Figure 7:
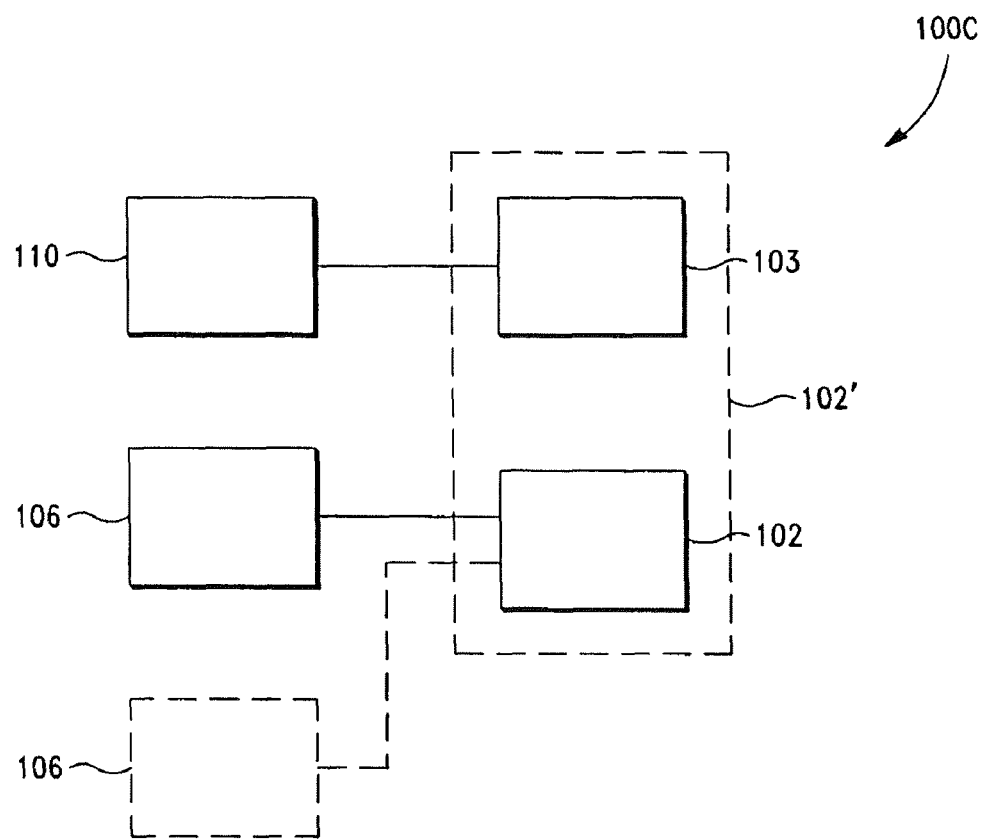
FIG. 7 is a schematic illustration of yet another embodiment of a taste modulation system, according to the invention.

Referring now to FIG. 7, there is shown yet another embodiment of a taste modulation system 100C of the invention. As illustrated in FIG. 7, the control system 100C similarly includes a control module 102 and a treatment member 106, As illustrated in FIG. 7, the system 100C includes at least one food intake sensor 110 that is adapted to monitor the food intake or consumption of a subject and generate at least one signal indicative of the food intake, i.e. food intake signal.

As one having ordinary skill in the art will appreciate, various sensing methods and sensors can be employed within the scope of the invention to monitor food intake. In one embodiment, the method for monitoring food intake comprises implanting one or more sensing electrodes in or at the esophagus to detect the passage of food as the subject swallows. The swallows are then summed over a predetermined time interval to estimate the amount of food consumed in that interval.

According to the invention, motion and pressure sensors, and other physiological devices, such as gastrointestinal bands that are adapted to sense pressure within a gastrointestinal tract structure or pressure changes caused by expansion or contraction of a gastrointestinal tract structure can also be employed.

The system 100C also includes a processing module (or computer) 103. According to the invention, the processing module 103 can be a separate component or a sub-system of a control module 102', as shown in phantom. The processing module 103 similarly preferably includes storage means adapted to store the captured neuro-electrical signals, food intake signals and generated confounding and simulated neuro-electrical signals.

In a preferred embodiment of the invention, the processor 36 includes storage means for storing the captured neuro-electrical signals and food intake signals. The processor 36 is further adapted to extract the components of the neuro-electrical signals and store the signal components in the storage means.

In a preferred embodiment, the control module 103 is programmed to (i) detect when food intake signals reflect that the subject has exceeded a predetermined threshold of food intake in a predetermined period of time or has not consumed sufficient food over a predetermined period of time, (ii) generate a confounding neuro-electrical signal, and (iii) generate simulated neuro-electrical signals that modulate the sense of taste and smell in the body.

The control module 103 is preferably further adapted to transmit the confounding neuro-electrical signal or simulated neuro-electrical signal to the subject in response to a food intake signal reflecting that the subject has exceeded a predetermined threshold of food intake in a predetermined period of time, a food intake signal reflecting that the subject has not consumed a predetermined threshold of food intake in a predetermined period of time, at a predetermined period of time (or time interval) and/or manually, i.e., upon activation of a first manual switch (not shown).

As illustrated in FIG. 7, the confounding neuro-electrical signals and simulated neuro-electrical signals are routed to a transmitter 106 that is adapted to be in communication with the subject's body. The transmitter 106 is adapted to transmit the confounding and simulated neuro-electrical signals and confounding satiety signals to the subject (in a similar manner as described above).

According to the invention, each of the systems 100A, 100B and 100C described above can include at least a second transmitter (shown in phantom and designated 108). By employing multiple transmitters, multiple simulated and/or confounding neuro-electrical signals can be transmitted to two or more different nerves or nerve complexes, whereby the senses of taste and smell can be substantially simultaneously modulated.

In accordance one embodiment of the invention, the method for modulating eating behavior of a subject thus includes the steps of (i) generating at least one confounding neuro-electrical signal that is adapted to modulate the sense of taste in the body, and (ii) transmitting the confounding neuro-electrical signal to the subject.

In one embodiment, the modulation comprises restricting the transmission of afferent information to the brain that is generated in the body and associated with the sense of taste.

In another embodiment, the modulation comprises substantially abating the transmission of afferent information to the brain that is generated in the body and associated with the sense of taste.

In one embodiment, the confounding neuro-electrical signal is transmitted to the subject at predetermined time intervals.

In one embodiment, the confounding neuro-electrical signal is transmitted to the subject manually.

In another embodiment, the confounding neuro-electrical signal is transmitted to the subject manually and at predetermined time intervals.

In yet another embodiment, a plurality of confounding neuro-electrical signals is transmitted to the subject.

In accordance with another embodiment of the invention, the method for modulating eating behavior of a subject includes the steps of (i) generating at least one simulated neuro-electrical signal that is adapted to modulate the sense of taste in the body, and (ii) transmitting the simulated neuro-electrical signal to the subject.

Preferably, the simulated neuro-electrical signal substantially corresponds to or is representative of a neuro-electrical signal that is generated in the body.

In one embodiment, the modulation comprises inducing the sense of taste in the subject's body.

In another embodiment, the modulation comprises enhancing the sense of taste in the subject's body.

In one embodiment, the simulated neuro-electrical signal is transmitted to the subject at predetermined time intervals.

In one embodiment, the neuro-electrical signal is transmitted manually to the subject.

In another embodiment, the simulated neuro-electrical signal is transmitted to the subject manually and at predetermined time intervals.

In yet another embodiment, a plurality of simulated neuro-electrical signals is transmitted to the subject.

In accordance with another embodiment of the invention, the method for modulating eating behavior of a subject includes the steps of (i) generating at least one confounding neuro-electrical signal that is adapted to modulate the sense of smell in the body, and (ii) transmitting the confounding neuro-electrical signal to the subject.

In one embodiment, the modulation comprises restricting the transmission of afferent information to the brain that is generated in the body and associated with the sense of smell.

In another embodiment, the modulation comprises substantially abating the transmission of afferent information to the brain that is generated in the body and associated with the sense of smell.

In one embodiment, the confounding neuro-electrical signal is transmitted to the subject at predetermined time intervals.

In one embodiment, the confounding neuro-electrical signal is transmitted to the subject manually.

In another embodiment, the confounding neuro-electrical signal is transmitted to the subject manually and at predetermined time intervals.

In yet another embodiment, a plurality of confounding neuro-electrical signals is transmitted to the subject.

In accordance with another embodiment of the invention, the method for modulating eating behavior of a subject includes the steps of (i) generating at least one simulated neuro-electrical signal that is adapted to modulate the sense of smell in the body, and (ii) transmitting the simulated neuro-electrical signal to the subject.

Preferably, the simulated neuro-electrical signal substantially corresponds to or is representative of a neuro-electrical signal that is generated in the body.

In one embodiment, the modulation comprises inducing the sense of smell in the subject's body.

In another embodiment, the modulation comprises enhancing the sense of smell in the subject's body.

In one embodiment, the simulated neuro-electrical signal is transmitted to the subject at predetermined time intervals, In one embodiment, the neuro-electrical signal is transmitted manually to the subject.

In another embodiment, the simulated neuro-electrical signal is transmitted to the subject manually and at predetermined time intervals.

In yet another embodiment, a plurality of simulated neuro-electrical signals is transmitted to the subject.

In another embodiment of the invention, the method for modulating eating behavior of a subject includes the steps of (i) generating at least one confounding neuro-electrical signal that is adapted to modulate the sense of taste in the body, (ii) sensing food intake in the subject over at least a first period of time, and (iii) transmitting the confounding neuro-electrical signal to the subject.

In one embodiment, the modulation comprises restricting the transmission of afferent information to the brain that is generated in the body and associated with the sense of smell.

In another embodiment, the modulation comprises substantially abating the transmission of afferent information to the brain that is generated in the body and associated with the sense of smell.

In one embodiment, the confounding neuro-electrical signal is transmitted to the subject if the food intake of the subject exceeds a predetermined threshold level during the first period of time.

In one embodiment, the confounding neuro-electrical signal is transmitted to the subject at predetermined time intervals.

In another embodiment, the confounding neuro-electrical signal is transmitted manually to the subject.

In yet another embodiment, a plurality of confounding neuro-electrical signals is transmitted to the subject.

In another embodiment of the invention, the method for modulating eating behavior of a subject includes the steps of (i) generating at least one simulated neuro-electrical signal that is adapted to modulate the sense of taste in the body, (ii) sensing food intake in the subject over at least a first period of time, and (iii) transmitting the simulated neuro-electrical signal to the subject.

Preferably, the simulated neuro-electrical signal substantially corresponds to or is representative of a neuro-electrical signal that is generated in the body.

In one embodiment, the modulation comprises inducing the sense of taste in the subject's body.

In another embodiment, the modulation comprises enhancing the sense of taste in the subject's body.

In one embodiment, the simulated neuro-electrical signal is transmitted to the subject if the food intake of the subject falls below a predetermined threshold level during the first period of time.

In one embodiment, the simulated neuro-electrical signal is transmitted to the subject at predetermined time intervals.

In another embodiment, the simulated neuro-electrical signal is transmitted manually to the subject.

In yet another embodiment, a plurality of simulated neuro-electrical signals is transmitted to the subject.

In another embodiment of the invention, the method for modulating eating behavior of a subject includes the steps of (i) generating at least one confounding neuro-electrical signal that is adapted to modulate the sense of smell in the body, (ii) sensing food intake in the subject over at least a first period of time, and (iii) transmitting the confounding neuro-electrical signal to the subject.

In one embodiment, the modulation comprises restricting the transmission of afferent information to the brain that is generated in the body and associated with the sense of smell.

In another embodiment, the modulation comprises substantially abating the transmission of afferent information to the brain that is generated in the body and associated with the sense of smell.

In one embodiment, the confounding neuro-electrical signal is transmitted to the subject if the food intake of the subject exceeds a predetermined threshold level during the first period of time.

In one embodiment, the confounding neuro-electrical signal is transmitted to the subject at predetermined time intervals.

In another embodiment, the confounding neuro-electrical signal is transmitted manually to the subject.

In another embodiment of the invention, the method for modulating eating behavior of a subject includes the steps of (i) generating at least one simulated neuro-electrical signal that is adapted to modulate the sense of smell in the body, (ii) sensing food intake in the subject over at least a first period of time, and (iii) transmitting the simulated neuro-electrical signal to the subject.

Preferably, the simulated neuro-electrical signal substantially corresponds to or is representative of a neuro-electrical signal that is generated in the body.

In one embodiment, the modulation comprises inducing the sense of smell in the subject's body.

In another embodiment, the modulation comprises enhancing the sense of smell in the subject's body.

In one embodiment, the simulated neuro-electrical signal is transmitted to the subject if the food intake of the subject falls below a predetermined threshold level during the first period of time.

In one embodiment, the simulated neuro-electrical signal is transmitted to the subject at predetermined time intervals.

In another embodiment, the simulated neuro-electrical signal is transmitted manually to the subject.

In yet another embodiment, a plurality of simulated neuro-electrical signals is transmitted to the subject.

In another embodiment of the invention, the method for modulating eating behavior of a subject includes the steps of (i) generating at least a first confounding neuro-electrical signal that is adapted to modulate the sense of taste in the body, (ii) generating at least a second confounding neuro-electrical signal that is adapted to modulate the sense of smell in the body, (iii) sensing food intake in the subject over at least a first period of time, and (iv) transmitting the first and second confounding neuro-electrical signals to the subject when the food intake of the subject exceeds a predetermined threshold level during the first period of time.

In another embodiment of the invention, the method for modulating eating behavior of a subject includes the steps of (i) generating at least a first simulated neuro-electrical signal that is adapted to modulate the sense of taste in the body, (ii) generating at least a second simulated neuro-electrical signal that is adapted to modulate the sense of smell in the body, (iii) sensing food intake in the subject over at least a first period of time, and (iv) transmitting the first and second simulated neuro-electrical signals to the subject when the food intake of the subject falls below a predetermined threshold level during the first period of time.

In each of the noted embodiments, the confounding and simulated neuro-electrical signals are transmitted to the subject's nervous system.

In some embodiments, confounding and simulated neuro-electrical signals adapted to modulate the sense of taste are transmitted to the subject's glossopharyngeal nerve.

In some embodiments, confounding and simulated neuro-electrical signals adapted to modulate the sense of smell are transmitted to the subject's Olfactory nerve complex.

In one embodiment of the invention, the step of transmitting a confounding or simulated neuro-electrical signal to the subject is accomplished by direct conduction or transmission through unbroken skin at a zone adapted to communicate with a target nerve, e.g., glossopharyngeal nerve. Such zone will preferably approximate a position close to the nerve or nerve plexus onto which the signal is to be imposed.

In an alternate embodiment of the invention, the step of transmitting a confounding or simulated neuro-electrical signal to the subject is accomplished by direct conduction via attachment of an electrode to the receiving nerve or nerve plexus. This requires a surgical intervention to physically attach the electrode to the selected target nerve.

In yet another embodiment of the invention, the step of transmitting a confounding or simulated neuro-electrical signal to the subject is accomplished by transposing the waveform signal into a seismic form in a manner that allows the appropriate "nerve" to receive and obey the coded instructions of the seismic signal.

According to the invention, a single confounding or simulated neuro-electrical signal or a plurality of confounding or simulated neuro-electrical signals can be transmitted to the subject in conjunction with one another.

The system for modulating eating behavior, in accordance with one embodiment of the invention, generally comprises (i) a processor adapted to generate at least one confounding or simulated neuro-electrical signal that is adapted to modulate the sense of taste in the body, and (ii) at least one signal transmitter adapted to be in communication with a subject's body for transmitting the confounding and simulated neuro-electrical signals to the subject.

In another embodiment of the invention, the system for modulating eating behavior comprises (i) a processor adapted to generate at least one confounding or simulated neuro-electrical signal that is adapted to modulate the sense of smell in the body, and (ii) a signal transmitter adapted to be in communication with a subject's body for transmitting confounding and simulated neuro-electrical signals to the subject.

In another embodiment of the invention, the system for modulating eating behavior comprises (i) at least a first food intake sensor adapted to monitor the food intake of a subject and provide at least a first food intake signal indicative of the food intake, (ii) a processor in communication with the food intake sensor adapted to receive the first food intake signal, the processor being further adapted to generate at least one confounding or simulated neuro-electrical signal that is adapted to modulate the sense of taste in the body, and (iii) a signal transmitter adapted to be in communication with the subject's body for transmitting confounding and simulated neuro-electrical signals to the subject.

In another embodiment of the invention, the system for modulating eating behavior comprises (i) at least a first food intake sensor adapted to monitor the food intake of a subject and provide at least a first food intake signal indicative of the food intake, (ii) a processor in communication with the food intake sensor adapted to receive the first food intake signal, the processor being further adapted to generate at least one confounding or simulated neuro-electrical signal that is adapted to modulate the sense of smell in the body, and (iii) a signal transmitter adapted to be in communication with the subject's body for transmitting confounding and simulated neuro-electrical signals to the subject.

As indicated above, in some embodiments, the system includes two signal transmitters that are adapted to transmit simulated neuro-electrical signals and confounding neuro-electrical signals to two different nerves and/or nerve complexes, whereby the senses of taste and smell can be substantially simultaneously modulated.

EXAMPLES

The following examples are given to enable those skilled in the art to more clearly understand and practice the present invention. They should not be considered as limiting the scope of the invention, but merely as being illustrated as representative thereof.

Example 1

A subject is presented that has an eating disorder. The subject also has a body mass index greater than forty.

The subject is referred to a nutritionist for nutritional counseling. The subject is also placed on an exercise regime.

The subject is also prescribed taste and smell modulation via a combined taste and smell modulation system of the invention.

A first signal transmitter is attached to the subject's glossopharyngeal nerve. A second signal transmitter is attached to the subject's intermediate nerve. A third signal transmitter is attached to the subject's Olfactory tract.

A first confounding neuro-electrical signal that is adapted to modulate the subject's sense of taste, i.e., substantially abate the transfer of afferent information associated with the sense of taste to the subject's brain, is generated by the system. A second confounding neuro-electrical signal that is adapted to modulate the subject's sense of smell, i.e., substantially abate the transfer of afferent information associated with the sense of smell to the subject's brain, is generated by the system.

The system is programmed to substantially simultaneously transmit the first and second confounding neuro-electrical signals to the subject via the first and second transmitters every 3 hours and upon manual activation, whereby the subject is rendered ageusic and anosimic and, hence, temporarily loses the desire to eat.

Example 2

A subject is presented that has an eating disorder, i.e. suffering from anorexia nervosa.

The subject is prescribed taste and smell modulation via a combined taste and smell modulation system of the invention. A first signal transmitter is attached to the subject's glossopharyngeal nerve. A second signal transmitter is attached to the subject's Olfactory tract.

A first simulated neuro-electrical signal that is adapted to modulate the subject's sense of taste, i.e., enhance the sense of taste, is generated by the system. A second simulated neuro-electrical signal that is adapted to modulate the subject's sense of smell, i.e., sense of smell is generated by the system.

The system is programmed to substantially simultaneously transmit the first and second simulated neuro-electrical signals to the subject via the first and second transmitters every 3 hours and upon manual activation, whereby the subject experiences a desire to eat.

As will be appreciated by one having ordinary skill in the art, the present invention has utility in a multitude of medical applications. Among the medical applications are the treatment of the following eating disorders:
Compulsive overeating
Obesity
Bulimia
Anorexia Nervosa
Ageusia
Anosmia Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for modulating eating behavior, comprising the steps of:
    generating at least one confounding neuro-electrical signal that is configured to modulate a sense of taste in a body, said at least one neuro-electrical signal comprising an electrical waveform signal that mimics a naturally occurring electrical signal in a nervous system of a body;

sensing food intake in a subject over at least a first period of time by implanting one or more sensing electrodes at an esophagus to detect a passage of food said subject swallows; and transmitting said at least one confounding neuro-electrical signal to said subject to modulate said eating behavior of said subject.

2. The method of claim 1, wherein said modulate comprises restricting the transmission of afferent information to said subject's brain that is generated in said subject's body and associated with the sense of smell.

3. The method of claim 1, wherein said modulate comprises substantially abating said transmission of afferent information to said subject's brain that is generated in said subject's body and associated with the sense of smell.

4. The method of claim 1, wherein said at least one confounding neuro-electrical signal is transmitted to said subject if said food intake of said subject exceeds a predetermined threshold level during said first period of time.

5. A method for modulating eating behavior, comprising the steps of:

generating at least one simulated neuro-electrical signal that is configured to modulate a sense of taste in a body, said at least one simulated neuro-electrical signal comprising an electrical waveform signal that mimics a naturally occurring electrical signal in a nervous system of a body;

sensing food intake in a subject over at least a first period of time by implanting one or more sensing electrodes at an esophagus to detect a passage of food said subject swallows; and transmitting said simulated neuro-electrical signal to said subject to modulate said eating, behavior of said subject.

6. The method of claim 5, wherein said at least one simulated neuro-electrical signal substantially corresponds to a neuro-electrical signal that is generated in the body.

7. The method of claim 5, wherein said at least one modulation comprises inducing said sense of taste in said subject's body.

8. The method of claim 5, wherein said modulation comprises enhancing said sense of taste in said subject's body.

9. The method of claim 5, wherein said at least one simulated neuro-electrical signal is transmitted to said subject if said food intake of said subject falls below a predetermined threshold level during said first period of time.

10. A method for modulating eating behavior, comprising the steps of:

generating at least one confounding neuro-electrical signal that is configured to modulate a sense of smell in a body, said at least one confounding neuro-electrical signal comprising an electrical waveform signal that mimics a naturally occurring electrical signal in a nervous system of a body;

sensing food intake in a subject over at least a first period of time by implanting one or more sensing electrodes at an esophagus to detect the passage of food said subject swallows; and transmitting said at least one confounding neuro-electrical signal to said subject to modulate an eating behavior of said subject.

11. The method of claim 10, wherein said subject. comprises restricting the transmission of afferent information to said subject's brain that is generated in said subject's body and associated with the sense of smell.

12. The method of claim 10, wherein said modulate comprises substantially abating said transmission of afferent information to said subject's brain that is generated in said subject's body and associated with the sense of smell.

13. The method of claim 10, wherein said at least one confounding neuro-electrical signal is transmitted to said subject if said food intake of said subject exceeds a predetermined threshold level during said first period of time.

14. A method for modulating eating behavior, comprising the steps of:

generating at least one simulated neuro-electrical signal that is configured to modulate a sense of smell in a body, said at least one simulated neuro-electrical signal comprising an electrical waveform signal that mimics a naturally occurring electrical signal in a nervous system of a body; sensing food intake in a subject over at least a first period of time by implanting one or more sensing electrodes at an esophagus to detect the passage of food said subject swallows; and transmitting said at least one simulated neuro-electrical signal to said subject to modulate an eating behavior of said subject.

15. The method of claim 14, wherein said at least one simulated neuro-electrical signal substantially corresponds to a neuro-electrical signal that is generated in the body.

16. The method of claim 14, wherein said nodulation comprises inducing said sense of smell in said subject's body.

17. The method of claim 14, wherein said modulation comprises enhancing said sense of smell in said subject's body.

18. The method of claim 14, wherein said at least one simulated neuro-electrical signal is transmitted to said subject if said food intake of said subject falls below a predetermined threshold level during said first period of time.

* * * * *